(12) United States Patent
Bergmann et al.

(10) Patent No.: US 7,989,169 B2
(45) Date of Patent: Aug. 2, 2011

(54) SELECTIVE AMPLIFICATION OF METHYLATED NUCLEIC ACIDS

(75) Inventors: Frank Bergmann, Iffeldorf (DE); Christine Markert-Hahn, Penzberg (DE)

(73) Assignee: Roche Molecular Systems, Inc., Pleasanton, CA (US)

( * ) Notice: Subject to any disclaimer, the term of this patent is extended or adjusted under 35 U.S.C. 154(b) by 644 days.

(21) Appl. No.: 11/658,569

(22) PCT Filed: Sep. 2, 2005

(86) PCT No.: PCT/EP2005/009475
§ 371 (c)(1),
(2), (4) Date: Jan. 24, 2007

(87) PCT Pub. No.: WO2006/024541
PCT Pub. Date: Mar. 9, 2006

(65) Prior Publication Data
US 2009/0208930 A1 Aug. 20, 2009

(30) Foreign Application Priority Data
Sep. 3, 2004 (EP) .................................. 04020974

(51) Int. Cl.
*C12Q 1/68* (2006.01)
*C12P 19/34* (2006.01)
(52) U.S. Cl. ...................................... 435/6.12; 435/91.1
(58) Field of Classification Search .................. None
See application file for complete search history.

(56) References Cited

U.S. PATENT DOCUMENTS

| | | | |
|---|---|---|---|
| 4,458,066 A | 7/1984 | Caruthers et al. | |
| 4,683,202 A | 7/1987 | Mullis et al. | |
| 5,130,238 A | 7/1992 | Malek et al. | |
| 5,137,806 A | 8/1992 | LeMaistre et al. | |
| 5,210,015 A | 5/1993 | Gelfand et al. | |
| 5,487,972 A | 1/1996 | Gelfand et al. | |
| 5,595,890 A | 1/1997 | Newton et al. | |
| 5,639,611 A | 6/1997 | Wallace et al. | |
| 5,683,896 A | 11/1997 | Hartley et al. | |
| 5,786,146 A | 7/1998 | Herman et al. | |
| 5,804,375 A | 9/1998 | Gelfand et al. | |
| 6,004,826 A | 12/1999 | Segev | |
| 6,174,670 B1 | 1/2001 | Wittwer et al. | |
| 6,180,344 B1 * | 1/2001 | Chen ............................. | 435/6 |
| 6,331,393 B1 | 12/2001 | Laird et al. | |
| 2003/0082600 A1 | 5/2003 | Olek et al. | |
| 2004/0146868 A1 | 7/2004 | Cottrell et al. | |
| 2005/0069879 A1 | 3/2005 | Berlin | |

FOREIGN PATENT DOCUMENTS

| | | |
|---|---|---|
| EP | 0 200 362 B1 | 12/1986 |
| EP | 0 201 184 B2 | 12/1986 |
| EP | 0 389 063 B1 | 9/1990 |
| EP | 0 401 037 B1 | 12/1990 |
| EP | 0 439 182 B1 | 7/1991 |
| EP | 0 415 755 B1 | 12/1995 |
| EP | 0 976 835 B1 | 2/2000 |
| EP | 1 394 173 A1 | 3/2004 |
| EP | 04020974.4 | 1/2005 |
| WO | WO 90/01069 A1 | 2/1990 |
| WO | WO 92/02638 A1 | 2/1992 |
| WO | WO 92/08808 A1 | 5/1992 |
| WO | WO 01/37291 A1 | 5/2001 |
| WO | WO 01/37291 A2 | 5/2001 |
| WO | WO 02/061124 * | 8/2002 |
| WO | WO 03/027259 A2 | 4/2003 |
| WO | WO 03/027259 A3 | 4/2003 |
| WO | WO 03/064701 A2 | 8/2003 |
| WO | WO 03/064701 A3 | 8/2003 |
| WO | WO 2004/067777 A1 | 8/2004 |
| WO | WO 2006/009870 A2 | 1/2006 |
| WO | WO 2006/009870 A3 | 1/2006 |
| WO | WO 2005/009475 | 3/2006 |
| WO | WO 2006/024541 A2 | 3/2006 |

OTHER PUBLICATIONS

Kornberg, Minireview DNA Replication, The Journal of Biological Chemistry, vol. 263, No. 1, Issue of Jan. 5, pp. 1-4, 1988.*
Ghoshal et al., Inhibitors of Histone Deacetylase and DNA Methyltransferase Synergistically Activate the Methylated Metallothionein I Promoter by Activating the Transcription Factor MTF-1 and Forming an Open Chromatin Structure, Molecular and Cellular Biology, Dec. 2002, p. 8302-8319 vol. 22, No. 23.*
Rein et al., Survey and Summary Identifying 5-methylcytosine and related modifications in DNA genomes,Nucleic Acids Research, 1998, vol. 26, No. 10 2255-2264.*
Klein et al., Comparative genomic hybridization, loss of heterozygosity, and DNA sequence analysis of single cells, Proc. Natl. Acad. Sci. USA, vol. 96, pp. 4494-4499, Apr. 1999.*
Sadri et al., Rapid analysis of DNA methylation using new restriction enzyme sites created by bisulfite modification, Nucleic Acids Research, 1996, vol. 24, No. 24, pp. 5058-5059.*
Abramson, R., et al, 1993, "Nucleic acid amplification technologies", *Current Opinion in Biotechnology*, 4: 41-47.
Abravaya, K., et al, 2005, "Strategies to Avoid Amplicon Contamination", *Abbott Laboratories*, 125-133.
Ausubel, F., et al., 2001, Current Protocols in Molecular Biology, vol. 1.
Ausubel, F., et al., 2001, Current Protocols in Molecular Biology, vol. 2.
Ausubel, F., et al., 2001, Current Protocols in Molecular Biology, vol. 3.
Barany, F., et al, 1991, "Genetic disease detection and DNA amplification using cloned thermostable ligase", *Proc. Natl. Acad. Sci. USA*, 88 189-193.
Barany, F., et al, 1991, "Review: The Ligase Chain Reaction in a PCR World", *PCR Methods and Applications*, 1: 5-16.
Beaucage, S., et al, 1981, "Deoxynucleoside Phosphoramidites—A New Class of Key Intermediates for Deoxypolynucleotide Synthesis", *Tetrahedron Letters*, 22 (20): 1859-1862.

(Continued)

*Primary Examiner* — Mark Staples
(74) *Attorney, Agent, or Firm* — Rhea Cyd Nersesian

(57) ABSTRACT

The invention is related to a method for amplifying a methylated target nucleic acid in a sample while avoiding amplification of a non-methylated target nucleic acid by inactivating it. This is accomplished by a restriction enzyme digest after bisulfite treatment of the target nucleic acid. The invention is further related to the use of a restriction enzyme to avoid amplification of a non-methylated target nucleic acid while amplifying a methylated target nucleic acid in a sample and kits for performing the methods according to the invention.

16 Claims, 4 Drawing Sheets

OTHER PUBLICATIONS

Benyajati, C., et al, 1980, "Alcohol dehydrogenase in *Drosophila*: isolation and characterization of messenger RNA and cDNA clone", *Nucleic Acids Research*, 8 (23) 5649-5667.

Brown, E., et al, 1979, "Chemical Synthesis and Cloning of a Tyrosine tRNA Gene", *Methods in Enzymology*, 68 109-151.

Cedar, H., et al, 1979, "Direct detection of methylated cytosine in DNA by use of the restriction enzyme MspI", *Nucleic Acids Research*, 6 (6): 2125-2132.

Chang, S., et al, 1992, "PCR Amplification Following Restriction to Detect Site-Specific DNA Methylation", *Plant Molecular Biology Reporter*, 10 (4) 362-366.

Clark, S., et al, 1994, "High Sensitivity Mapping of Methylated Cytosines", *Nucleic Acids Research*, 22 (15) 2990-2997.

Clark, S., et al, 1997, "Bisulphite Genomic Sequencing of Methylated Cytosines", Detection of Mutations and Polymorphisms in DNA, Chapter 14, pp. 151-162, CRC Press, Inc.

Feil, R., et al, 1994, "Methylation analysis on individual chromosomes: improved protocol for bisulphate genomic sequencing", *Nucleic Acids Research*, 22 (4): 695-696.

Fojtová, M., et al, 2001, "Cytosine methylation of plastid genome in higher plants, Fact or artifact?", *Plant Science*, 160 585-593.

Frommer, M., et al, 1992, "A genomic sequencing protocol that yields a positive display of 5-methylcytosine residues in individual DNA strands", *Proc. Natl. Acad. Sci. USA*, 89: 1827-1831.

Gait, M., 1984, "Oligonucleotide Synthesis, A Practical Approach", ISBN 0-904147-74-6, IRL Press, Oxford, England.

Garegg, P., et al, 1985, "Formation of Internucleotidic bonds via Phosphonate Intermediates", *Chemica Scripta*, 25: 280-282.

Grigg, G., 1994, "Sequencing 5-Methylcytosine Residues in Genomic DNA", *BioEssays*, 16 (6): 431-436.

Grigg, G., 1996, "Sequencing 5-methylcytosine residues by the bisulphate method", *DNA Sequence—The Journal of Sequencing and Mapping*, 6: 189-198.

Grunau, C., 2001, "Bisulfite genomic sequencing: systematic investigation of critical experimental parameters", *Nucleic Acids Research*, 29 (13 e65): 1-7.

Guatelli, J., et al, 1990, "Isothermal, in vitro amplification of nucleic acids by a multienzyme reaction modeled after retroviral replication", *Proc. Natl. Acad. Sci. USA*, 87: 1874-1878.

Ki-Hyo, J., et al, 2001, "Identification of a Sequence Containing Methylated Cytidine in *Corynebacterium glutamicum* and *Brevibacterium flavum* Using Bisulfite DNA Derivatization and Sequencing", *J. Microbiol. Biotechnol*, 11 (5): 819-824.

Klaschik, S., et al, 2002, "Comparison of Different Decontamination Methods for Reagents to Detect Low Concentrations of Bacterial 16S DNA by Real-Time-PCR", *Molecular Biotechnology*, 22: 231-242.

Komiyama, M., et al, 1994, "Catalysis of Diethylenetriamine for Bisulfite-Induced Deamination of Cytosine in Oligodeoxyribonucleotides", *Tetrahedron Letters*, 35 (44): 8185-8188.

Kupper, D., et al, 1997, "Reliable Detection of DNA GpG Methylation Profiles by the Isoschizomers MspI/HpaII Using Oligonucleotide Stimulators", *Biotechniques*, 23 (5): 843-846.

Kwoh, D., et al, 1989, "Transcription-based amplification system and detection of amplified human immunodeficiency virus type 1 with a bead-based sandwich hybridization format", *Proc. Natl. Acad. Sci. USA*, 86: 1173-1177.

Narang, S., et al, 1979, "Improved Phosphotriester method for the Synthesis of Gene Fragments", *Methods in Enzymology*, 68: 90-98.

Oakeley, E., 1999, "DNA methylation analysis: a review of current methodologies", *Phamacology & Therapeutics*, 84: 389-400.

Olek, A., et al, 1996, "A medofied and improved method for bisulphate based cytosine methylatiohn analysis", *Nucleic Acids Research*, 24 (24): 5064-5066.

Paulin, R., et al, 1998, "Urea improves efficiency of bisulphate-mediated sequencing of 5'-methylcytosine in genomic DNA", *Nucleic Acids Research*, 26 (21): 5009-5010.

Pogribny, I., et al, 1999, "A Sensitive New Method for Rapid Detection of Abnormal Methylation Patterns in Global DNA and within CpG Islands", *Biochemical and Biophysical Research Communications*, 262, 624-628.

Raizis, A., et al, 1995, "A Bisulfite Method of 5-Methylcytosine Mapping That Minimizes Template Degradation", *Analytical Biochemistry*, 226, 161-166.

Sadri, R., et al, 1996, "Rapid analysis of DNA methylation using new restriction enzyme sites created by bisulfite modification", *Nucleic Acids Research*, 24 (24): 5058-5059.

Singer-Sam, J., et al, 1990, "A quantitative HpaII-PCR assay to measure methylation of DNA from a small number of cells", *Nucleic Acids Research*, 18 (3): 68.

Thornton, C., et al, 1992, "Utilizing Uracil DNA Glycosylase to Control Carryover Contamination in PCR: Characterization of Residual UDG Activity Following Thermal Cycling", *BioTechniques*, 13, (2): 180-183.

Wu, D., et al., 1989, "The Ligation Amplification Reaction (LAR)—Amplification of Specific DNA Sequences Using Sequential Rounds of Template-Dependent Ligation", *Genomics*, 4: 560-569.

Xiong, Z., et al., 1997, "Cobra: a sensitive and quantitative DNA methylation assay," *Nucleic Acids Research*, 25 (12): 2532-2534.

Youssoufian, H, et al., 1981, "Letter to the Editor: Setection of Mthylated Sequences in Eukaryotic DNA with the Restriction Endonucleases *Sma*1 and *Xma*1", *J. Mol. Biol.* 150: 133-136.

Rand, Keith, et al., 2002, "Conversion-specific detection of DNA methylation using real-time polymerase chain reaction (ConLight-MSP) to avoid false positives", Methods, 27:114-120.

Sasaki, Masahiro, et al., 2003, "Bisulfite conversion-specific and methylation-specific PCR: a sensitive technique for accurate evaluation of CpG methylation", Biochemical and Biophysical Research Communications, 309:305-309.

\* cited by examiner

SELECTIVE AMPLIFICATION OF METHYLATED NUCLEIC ACIDS

The present application claims the benefit of EP Appl. No. 04020974.4 filed Sep. 3, 2004, the content of which is hereby incorporated herein by reference in its entirety.

BACKGROUND OF THE INVENTION

1. Field of the Invention

The invention is related to a method for amplifying a methylated target nucleic acid in a sample while avoiding amplification of a non-methylated target nucleic acid by inactivating it. This is accomplished by a restriction enzyme digest after bisulfite treatment of the target nucleic acid. The invention is further related to the use of a restriction enzyme to avoid amplification of a non-methylated target nucleic acid while amplifying a methylated target nucleic acid in a sample and kits for performing the methods according to the invention.

2. Description of the Related Art

Genes constitute only a small proportion of the total mammalian genome, and the precise control of their expression in the presence of an overwhelming background of noncoding deoxyribonucleic acid (DNA) presents a substantial problem for their regulation. Noncoding DNA, containing introns, repetitive elements, and potentially active transposable elements requires effective mechanisms for its long term silencing. Mammals appear to have taken advantage of the possibilities afforded by cytosine methylation to provide a heritable mechanism for altering DNA-protein interactions to assist in such silencing. DNA methylation is essential for the development of mammals; and plays a potential role during aging and cancer. The involvement of methylation in the regulation of gene expression and as an epigenetic modification marking imprinted genes is well established. In mammals, methylation occurs only at cytosine residues and more specifically only on cytosine residues adjacent to a guanosine residue, i.e. at the sequence CG. The detection and mapping of DNA methylation sites are essential steps towards understanding the molecular signals which indicate whether a given sequence is methylated.

This is currently accomplished by the so-called bisulfite method described by Frommer, M., et al., Proc. Natl. Acad. Sci. USA 89 (1992) 1827-1831 for the detection of 5-methylcytosines. The bisulfite method of mapping 5-methylcytosine uses the effect that sodium hydrogen sulfite reacts with cytosine but not or only poorly with 5-methyl-cytosine. Cytosine reacts with bisulfite to form a sulfonated cytosine reaction intermediate being prone to deamination resulting in a sulfonated uracil which can be desulfonated to uracil under alkaline conditions. It is common knowledge that uracil has the base pairing behavior of thymine different to the educt cytosine whereas 5-methylcytosine has the base pairing behavior of cytosine. This makes the discrimination of methylated or non-methylated cytosines possible by e.g. bisulfite genomic sequencing (Grigg, G., and Clark, S., Bioessays 16 (1994) 431-436; Grigg, G. W., DNA Seq. 6 (1996) 189-198), methylation specific PCR (MSP) disclosed in U.S. Pat. No. 5,786,146 or by the use of blocking probes in PCR reactions (WO2002/072880). Oakeley, E. J., (Pharmacology & Therapeutics 84 (1999) 389-400. DNA methylation analysis: a review of current methodologies) reviews current methodologies of DNA methylation analysis.

There are various documents addressing specific aspects of the bisulfite reaction (Benyajati, C., et al., Nucleic Acids Res. 8 (1980) 5649-5667) make general investigations to the bisulfite modification of 5-methyl-deoxycytosine and deoxycytosine. Olek, A., et al., Nucleic Acids Res. 24 (1996) 5064-5066 disclose a method for bisulfite base sequencing whereby bisulfite treatment and subsequent PCR steps are performed on material embedded in agarose beads. In the bisulfite method as disclosed by Clark, S. J., et al., Nucleic Acids Res. 22 (1994) 2990-2997, the sample is desalted after deamination. Raizis, A. M., et al., Anal. Biochem. 226 (1995) 161-166 disclose a bisulfite method of 5-methylcytosine mapping that minimizes template degradation. They investigate the influence of pH, temperature and time of reaction. Similar investigations have been made by Grunau, C., et al., Nucleic Acids Res. 29 (2001) E65-5 or Warnecke, P. M., et al., Methods 27 (2002) 101-107. Different additional components in the bisulfite mixture are disclosed by WO 01/98528 or by Paulin, R. et al., Nucleic Acids Res. 26 (1998) 5009-5010. An additional bisulfite step after bisulfite treatment and PCR is disclosed in WO 02/31186. Komiyama, M., and Oshima, S., Tetrahedron Letters 35 (1994) 8185-8188 investigate the catalysis of bisulfite-induced deamination of cytosine in oligodeoxyribonucleotides. A specific bisulfite protocol is disclosed by WO 2004/067545. A variation of the bisulfite genomic sequencing method is disclosed by Feil, R., et al., Nucleic Acids Res. 22 (1994) 695-696, whereby the genomic DNA is bound to glass beads after deamination and washed. After elution the nucleic acid is desulfonated. EP 1 394 173 discloses a bisulfite method whereby the DNA is bound to the glass surface of a solid phase. Kits for performing bisulfite treatments are commercially available from Intergen, distributed by Serologicals Corporation, Norcross, Ga., USA, e.g. CpGenome™ DNA modification kit. The polymerase chain reaction (PCR) as described in U.S. Pat. No. 4,683,202 is also used in the field of the analysis of methylated nucleic acids. This method is even able to amplify analyte nucleic acids, e.g. of HCV, that are present in the smallest concentrations to such an extent that they become accessible to those nucleic acid tests which have been restricted to highly concentrated analytes. However, over time it has turned out that the laboratories in which the amplifications were carried out have in the meantime already become so strongly contaminated with the amplified nucleic acids that tests in samples which in fact do not contain the low concentrated nucleic acid at all lead to false-positive results since the samples have become contaminated by the environment with nucleic acids from previous amplifications (cross-contaminations). The high sensitivity of the amplification-based nucleic acid tests enables the detection of even the slightest contaminations and hence simulates the presence of the analyte in the sample (false-positive results).

EP-A-0 401 037 describes a method which partially remedies the described deficiency. In this method mononucleotides that are not naturally present in the nucleic acid to be detected are incorporated during the amplification into the amplificate of each analyte nucleic acid. Before a subsequent amplification is carried out, the sample together with the reagents used are subjected to a pretreatment in which all imported amplificates from earlier amplifications are enzymatically degraded. Uracil-N-glycosylase (UNG) is an example of a degradation reagent and dUTP is an example of a modified building block for the amplificates. An alternative method utilizes primers containing uracil instead of mononucleotides containing uracil. Such a method in which the primer binding sites are degraded on amplificates generated earlier is described in EP-A-0 415 755.

The mechanism of this decontamination method is based on the specific recognition of uracil-containing amplificates which are degraded by the enzyme. In the preparation of the amplification reaction UNG is added to the sample and usually already together with the master mix which contains all reagents necessary for the amplification. The aforementioned degradation reaction takes place in a brief incubation step before the subsequent amplification. If the reaction mixture is subsequently heated to a temperature above ca. 40° C., then UNG is inactivated. This is necessary to ensure that the UNG does not degrade the newly synthesized DNA which accumulates during the course of the amplification.

There are several documents disclosing further methods on the decontamination of mixtures used for this type of reaction. Klaschik, S. et al. (Molecular Biotechnology 22 (2002) 231-242. Comparison of different decontamination methods for reagents to detect low concentrations of bacterial 16S DNA by real-time PCR) disclose a comparison of decontamination methods using restriction enzyme cleavage compared with other methods. There is no methylation-specific cleavage and not in combination with bisulfite method. Only a DNAse digestion and not a restriction enzyme digestion was regarded to be effective. Abravaya, K. et al. (Lee, H. H. et al. (Ed.), Nucleic Acid Amplification Technologies 1997, 125-133. Strategies to avoid amplicon contamination) review techniques developed to prevent carryover contamination by contaminant DNA in DNA amplification procedures. The review includes pre-amplification decontamination using endonucleases but there is no disclosure of bisulfite modification or use thereof in methylation detection. U.S. Pat. No. 5,683,896 discloses another process for controlling contamination of nucleic acid and amplification reactions. US 2004/0005555 discloses the detection of bacteremia in emergency department patients at risk for infective endocarditis using universal 16S rRNA primers in a decontaminated PCR assay. The background DNA present in all PCR reagents is eliminated using a restriction endonuclease AluI digestion having multiple digestion sites in the amplicon but not in the primer sets. The restriction enzyme AluI enzyme is inactivated by heating to a temperature which inactivates AluI but not Taq polymerase. The method is not disclosed in combination with the bisulfite method and cannot be used when target DNA is present. DeFilippes, F. M. (Biotechniques 10 (1991) 26-30. Decontaminating the polymerase chain reaction) discloses the addition of template DNA to a modified PCR mixture to simulate contamination. The template DNA was inactivated by restriction enzyme digestion. After inactivation of restriction enzymes additional DNA template, buffer and Taq polymerase were added to the reaction and PCR proceeded. Limitations of this method are discussed. There is no disclosure of the bisulfite treatment or restriction enzyme digestion.

Several documents describe the general combination of bisulfite technology and restriction enzyme cleavage in the field of detection of methylated nucleic acids. Sadri, R. et al. (Nucleic Acids Res. 24 (1996) 5058-5059, Rapid analysis of DNA methylation using new restriction enzyme sites created by bisulfite modification) disclose the bisulfite treatment of DNA and subsequent amplification. Changes in restriction enzyme sites are detected. Velinov, M. et al. (Methods in Molecular Biology 217 (2003) 209-216, PCR-based strategies for the diagnosis of Pradet-Willi/Angelman syndromes) disclose a PCR-based methylation test using methylation-specific digestion of the amplified, bisulfite-treated DNA. Velinov, M. et al. (Molecular Genetics and Metabolism 69 (2000) 81-83. The feasibility of PCR-based diagnosis of Prader-Willi and Angelman syndromes using restriction analysis after bisulfite modification of genomic DNA) disclose a PCR-based methylation test using methylation-specific digestion of the amplified, bisulfite-treated DNA. Xiong, Z. et al. (Nucleic Acids Res. 25 (1997) 2532-2534. COBRA: a sensitive and quantitative DNA methylation assay) uses restriction enzyme digestion to reveal methylation-dependent sequence differences in PCR products of sodium bisulfite treated DNA. WO2003/000926 discloses the bisulfite treatment of DNA and subsequent amplification. Thereafter, the amplificate is digested with restriction endonucleases. The enzyme resistant fraction of digested DNA is then amplified in a further PCR. In all these documents, restriction enzyme cleavage is performed after PCR amplification.

Several other documents describe restriction enzyme digestions in connection with the bisulfite method. Fojtova, M. et al. (Plant Science 160 (2001) 585-593. Cytosine methylation of plastid genome in higher plants. Fact or artifact?) disclose bisulfite genomic sequencing performed on EcoRII-restricted DNA difference. The restriction enzyme digestion is performed before bisulfite treatment. Clark, S. J. et al. (Ed. G. R: Taylor, Laboratory Methods for the Detection of Mutations and Polymorphisms in DNA (1997) 151-162, Publisher CRC, Boca Raton, Fla.) review current methods available for the study of cytosine methylation in genomic DNA. The restriction enzyme digestions and the bisulfite method are described independently similarly to WO2003/064701. Jang, K.-H. et al. (J. Microbiology and Biotechnology 11 (2001) 819-824. Identification of a sequence containing methylated cytidine in *Corynebacterium glutamicum* and *Brevibacterium flavum* using bisulfite DNA derivatization and sequencing) disclose the bisulfite treatment of DNA and subsequent amplification, restriction enzyme digestion to remove not fully converted DNA and another round of amplification. Then, the DNA sequence is determined.

Other documents describe the use of restriction enzyme digests for the analysis of methylations. Kaneda, S. A. et al. (Molecular Medicine 39 (2002) 824-832) review various methods for analysis of DNA methylation including restriction enzyme digestions. WO2003/027259 discloses assays for detecting DNA methylation associated with diseases in mouse and their use in diagnosis. The technique to detect the extent of DNA methylation entails generating DNA fragments of a test sample by cleaving at methylation sites that are not methylated while sparing methylation sites in the DNA that are methylated. The method is not used in combination with the bisulfite method. Moore, T. (Methods in Molecular Biology 181 (2002) 193-203. Southern analysis using methyl-sensitive restriction enzymes) discloses the use of methyl-sensitive restriction enzymes and Southern analysis but not in combination with the bisulfite method. EP 0 976 835 discloses the detection of nucleic acid methylation using amplification fragment length polymorphism which is not used in combination with the bisulfite method. Pogribny, I. et al. (Biochem. Biophys. Res. Commun. 262 (1999) 624-628. Sensitive new method for rapid detection of abnormal methylation patterns in global DNA and within CpG islands) disclose a method based on the use of methylation-sensitive restriction endonucleases that leave a 5'-guanine overhang after DNA cleavage, with subsequent single nucleotide extension with radiolabeled [3H]dCTP. The method is not combined with the bisulfite method or PCR amplification. Kupper, D. et al. (Biotechniques 23 (1997) 843-847. Reliable detection of DNA CpG methylation profiles by the isoschizomers MspI/HpaII using oligonucleotide stimulators) disclose a protocol for detecting CpG methylation by the isoschizomeric restriction endonucleases MspI/HpaII but not in combination with the bisulfite method. Watts, G. S. et al. (Nucleic Acids Res. 23 (1995) 4740-4741. Detecting differences in 5-methylcytosine using restriction enzyme isoschizomers: an endogenous control for complete digestion) disclose the southern blot analysis of genomic DNA cut with methylation-sensitive isoschizomers like MspI/HpaII but not in combination with the bisulfite method. Chang, S. et al. (Plant Molecular Biology Reporter 10 (1992) 362-366. PCR amplification following restriction to detect site-specific methylation) disclose a procedure to test for DNA methylation at sites recognized by methylation-sensitive restriction endonucleases. The procedure is based on the assumption that PCR will amplify sequences between two primers only if target DNA is intact after digestion. The method is not used in combination with the bisulfite method. Szyf, M. et al. (Nucleic Acids Res. 10 (1982) 7247-7259. Studies on the biological role of DNA methylation: V—The pattern of *E. coli* DNA methylation) disclose an analysis of the state of the methylation of GATC sites in newly replicating DNA using the restriction enzyme DpnI but not in combination with the bisulfite method. Youssoufian, H. et al. (J. Mol. Biol. 150 (1981) 133-136). Detection of methylated sequences in eukaryotic DNA with the restriction endonucleases SmaI and XmaI) disclose two isoschizomers which either digest specific CpG sites methyl-sensitively or not. The restriction enzymes are not used in combination with the bisulfite method. Cedar, H. et al. (Nucleic Acids Res. 6 (1979) 2125-2132. Direct detection of methylated cytosine in DNA by use of restriction enzyme MspI) disclose the analysis of the state of methylation of CCGG sites using MspI/HpaII restriction enzymes and subsequent gel analysis but not in combination with the bisulfite method.

SUMMARY OF THE INVENTION

The widely-used method for decontamination of PCR mixtures by employing uracil-N-glycosylase cannot be used together with the bisulfite method which generates uracil from cytosine bases. Therefore, there is a need to provide a method that can be used for the decontamination of PCR mixtures in the field of the detection of methylated nucleic acids to avoid false positive results by the detection of contaminating nucleic acids.

Therefore, it is an object of the invention to provide a method which digests non-methylated target nucleic acid after the bisulfite treatment of DNA that can lead to wrong results. In more detail, an embodiment of the invention is a method for amplifying a methylated target nucleic acid in a sample while avoiding amplification of a non-methylated target nucleic acid whereby the methylated target nucleic acid comprises a nucleotide with a methylcytosine base in the recognition nucleic acid sequence of a restriction enzyme wherein the recognition nucleic acid sequence is in the amplified reaction product, the method comprising the steps of:
  (a) converting a non-methylated cytosine base in the methylated target nucleic acid in the sample into an uracil base while not converting the methylcytosine base;
  (b) adding a restriction enzyme to the sample which digests the non-methylated target nucleic acid whereby the methylated target nucleic acid is not digested by the restriction enzyme;
  (c) inactivating the restriction enzyme; and
  (d) amplifying the methylated target nucleic acid.

In another embodiment, the invention is related to a method for controlling contamination in sequential target nucleic acid amplification processes comprising a first and a second nucleic acid amplification process to amplify a target nucleic acid in a first and second sample, respectively, which comprises carrying out the first nucleic acid amplification process on the target nucleic acid sequence in the first sample prior to carrying out the second amplification process on the target nucleic acid in the second sample according to the invention.

In another embodiment of the invention, a restriction enzyme is used to digest non-methylated target nucleic acid in a sample comprising a methylated target nucleic acid that was not present in the sample during the conversion of a non-methylated cytosine base in the methylated target nucleic acid into an uracil base while not converting the methylcytosine.

In another embodiment of the invention, a restriction enzyme is used to avoid amplification of a non-methylated target nucleic acid present in a sample while amplifying a methylated target nucleic acid present in the sample.

In another embodiment of the invention, a kit is provided comprising a restriction enzyme, a compound comprising sulfite ions and a solid phase comprising a glass surface.

In another embodiment of the invention, a kit is provided comprising a restriction enzyme, a compound comprising sulfite ions, a solid phase comprising a glass surface, a pair of primers, a probe and a DNA polymerase.

A "nucleic acid" is a polymeric compound of "nucleotides" as known to the expert skilled in the art. It is used herein to denote a "nucleic acid" in a sample which should be analyzed, i.e. the presence, non-presence or amount thereof in a sample should be determined. Therefore, in other words the "nucleic acid" is the target and can therefore be also denoted as "target nucleic acid". For example, if it has to be determined whether blood contains the human immunodeficiency virus, the "target nucleic acid" is the nucleic acid of the human immunodeficiency virus or more specifically the nucleic acid sequence, i.e. the order of the bases adenine, guanine, cytosine or thymine, that is determined. More specifically in the context of the invention, the "target nucleic acid" is genomic DNA that may comprise methylated-cytosine bases in CpG sites. After "bisulfite treatment" the nucleic acid sequence of the genomic DNA is changed depending on methylation as non-methylated bases are converted to uracil bases and the changed nucleic acid sequence is determined.

The "methylated target nucleic acid" is according to the invention a target nucleic acid that comprises (after bisulfite treatment) a nucleotide with a methylated cytosine base in the recognition nucleic acid sequence of a restriction enzyme, particularly the restriction enzyme used in the present invention, more specifically the restriction enzyme chosen or used in step (b) of the method. The "non-methylated target nucleic acid" is according to the invention a "target nucleic acid" that comprises a nucleotide with a (non-methylated) cytosine base in the recognition nucleic acid sequence of a restriction enzyme, particularly the restriction enzyme used in the present invention, more specifically the restriction enzyme chosen or used in step (b) of the method. As understood by the invention, the "non-methylated target nucleic acid" may even comprise a nucleotide with a methylcytosine base but not in the recognition nucleic acid sequence of a restriction enzyme, particularly the restriction enzyme used in the present invention, more specifically the restriction enzyme chosen or used in step (b) of the method. The nucleic acid sequence of the "non-methylated target nucleic acid" is identical to the "methylated target nucleic acid" and the said nucleic acid molecules only differ in their methylation of a cytosine base or cytosine bases not affecting hydrogen bonding to complementary nucleic acids. According to the invention, the "non-methylated target nucleic acid" is a "contaminating nucleic acid" or "contaminating target nucleic acid" that makes the sample impure or pollutes the sample. It should not be present in the amplification step of the method as it may lead to false results.

As is known in the art, a "nucleoside" is a base-sugar combination. The base portion of the nucleoside is normally a heterocyclic base. The two most common classes of such heterocyclic bases are the purines and the pyrimidines, in more detail the adenine (A), guanine (G), thymine (T) or cytosine (C) base. The uracil base is naturally contained in the ribonucleic acid. Another naturally occurring base is 5-methyl-cytosine or methyl-cytosine, which is cytosine which is substituted by a methyl group at the 5-position of the aromatic ring of the base.

"Nucleotides" are "nucleosides" that further include a phosphate group covalently linked to the sugar portion of the nucleoside. For those "nucleosides" that include a pentofuranosyl sugar, the phosphate group can be linked to either the 2', 3' or 5' hydroxyl moiety of the sugar. A "nucleotide" is the "monomeric unit" of an "oligonucleotide", more generally denoted herein as an "oligomeric compound", or a "polynucleotide", more generally denoted as a "polymeric compound". Another general expression therefore is deoxyribonucleic acid (DNA) and ribonucleic acid (RNA).

According to the invention, an "oligomeric compound" is a compound consisting of "monomeric units" which may be "nucleotides" alone or "non-natural compounds" (see below), more specifically "modified nucleotides" (or "nucleotide analogs") or "non-nucleotide compounds", alone or combinations thereof. "Oligonucleotides" and "modified oligonucleotides" (or "oligonucleotide analogs") are subgroups of "oligomeric compounds" in the context of the invention.

In the context of this invention, the term "oligonucleotide" refers to "polynucleotides" formed from a plurality of "nucleotides" as the "monomeric unit", i.e. an "oligonucleotide" belongs to a specific subgroup of a "oligomeric compound" or "polymeric compound" of ribonucleic acid (RNA) or deoxyribonucleic acid (DNA) with "monomeric units". The phosphate groups are commonly referred to as forming the internucleoside backbone of the "oligonucleotide". The normal linkage or backbone of RNA and DNA is a 3' to 5' phosphodiester linkage.

"Oligonucleotides" and "modified oligonucleotides" (see below) according to the invention may be synthesized as principally described in the art and known to the expert in the field. Methods for preparing oligomeric compounds of specific sequences are known in the art, and include, for example, cloning and restriction of appropriate sequences and direct chemical synthesis. Chemical synthesis methods may include, for example, the phosphotriester method described by Narang, S. A., et al., Methods Enzymol. 68 (1979) 90-98, the phosphodiester method disclosed by Brown, E. L., et al., Methods Enzymol. 68 (1979) 109-151, the phosphoramidite method disclosed in Beaucage, S. L., and Caruthers, M. H., Tetrahedron Lett. 22 (1981) 1859-1862, the H-phosphonate method disclosed in Garegg, P. J., et al., Chem. Scr. 25 (1985) 280-282 and the solid support method disclosed in U.S. Pat. No. 4,458,066.

As said above, a "nucleic acid" as well as the "target nucleic acid" is a polymeric compound of "nucleotides" as known to the expert skilled in the art. It is used herein to denote a "nucleic acid" in a sample which should be analyzed, i.e. the presence, non-presence or amount thereof in a sample should be determined.

The term "primer" is used herein as known to the expert skilled in the art and refers to "oligomeric compounds" primarily to "oligonucleotides" but also to "modified oligonucleotides" that are able to "prime" DNA synthesis by a template-dependent DNA polymerase, i.e. the 3'-end of the e.g. oligonucleotide provides a free 3'-OH group whereto further "nucleotides" may be attached by a template-dependent DNA polymerase establishing 3' to 5' phosphodiester linkage whereby deoxynucleoside triphosphates are used and whereby pyrophosphate is released. Therefore, there is—except for the intended function—no fundamental difference between a "primer", an "oligonucleotide" or a "probe" according to the invention.

The term "probe" refers to synthetically or biologically produced nucleic acids (DNA or RNA) which, by design or selection, contain specific nucleotide sequences that allow them to hybridize under defined predetermined stringencies specifically (i.e., preferentially) to "target nucleic acids". A "probe" can be identified as a "capture probe" meaning that it "captures" the target nucleic acid so that it can be separated from undesirable materials which might obscure its detection. Once separation is accomplished, detection of the captured "target nucleic acid" can be achieved using a suitable procedure. "Capture probes" are often already attached to a solid phase. A specific example therefore is the microarray situation wherein a multitude of "capture probes" are attached to a "solid phase" which "capture" labeled cRNA or cDNA.

According to the invention the term a "bisulfite reaction", "bisulfite treatment" or "bisulfite method" shall mean a reaction for the conversion of a cytosine base, in particular cytosine bases, in a nucleic acid to an uracil base, or bases, preferably in the presence of bisulfite ions whereby preferably 5-methyl-cytosine bases are not significantly converted. This reaction for the detection of methylated cytosines is described in detail by Frommer et al., supra and Grigg and Clark, supra. The bisulfite reaction contains a deamination step and a desulfonation step (see FIG. 1; Grigg and Clark, supra). The statement that 5-methyl-cytosine bases are not significantly converted shall only take the fact into account that it cannot be excluded that a small percentage of 5-methyl-cytosine bases is converted to uracil although it is intended to convert only and exclusively the (non-methylated) cytosine bases (Frommer et al., supra).

The terms "methyl-cytosine base", "methylcytosine base", "methylated cytosine base" and "5-methyl-cytosine base" are used interchangeably throughout the application and shall denote the derivative of a cytosine base whereby a methyl group is attached to the C5 atom of the cytosine ring. A cytosine base is shown in the left part of FIG. 1. The term "non-methylated cytosine base" shall denote an underivatized cytosine base whereby no methyl group is attached to the C5 atom of the cytosine ring in contrast to the "methyl-cytosine base".

"Restriction enzymes" are endonucleases (restriction endonucleases) that are capable of recognizing a specific nucleotide or nucleic acid sequence in a deoxyribonucleic acid (DNA) molecule and cleaving the double-stranded DNA at specific sites. According to the invention, the "recognition nucleic acid sequence of a restriction enzyme" is the specific nucleic acid sequence recognized by the restriction enzyme. The restriction enzymes recognize specific short DNA sequences four to eight nucleotides long, and cleave DNA at a site within this sequence. In the context of the present disclosure, restriction enzymes may be used to cleave DNA molecules at sites corresponding to various restriction-enzyme recognition sites. Bacteria contain over 400 such enzymes that recognize and cut over 100 different DNA sequences. An isoschisomer (isoschizomer, isoschisomere, isoschizomere) is one of several restriction enzymes or endonucleases which are isolated from different sources but which break a DNA molecule at the same recognition site "Digestion" of DNA refers to catalytic "cleavage" of the DNA with a restriction enzyme that acts only at certain sequences in the DNA. The various restriction enzymes used herein are commercially available and their reaction conditions, cofactors and other requirements are used as would be known to the ordinarily skilled artisan.

The term "restriction site" refers to a "recognition (nucleic acid) sequence" or "restriction nucleic acid sequence" that is necessary for the manifestation of the action of a restriction enzyme, and includes a site of catalytic cleavage. When an enzyme (e.g. a restriction enzyme) is said to "cleave" a polynucleotide or nucleic acid, it is understood to mean that the restriction enzyme catalyzes or facilitates a cleavage of a polynucleotide or nucleic acid.

DETAILED DESCRIPTION OF THE INVENTION

Conventional techniques of molecular biology and nucleic acid chemistry, which are within the skill of the art, are explained in the literature. See, for example, Sambrook, J., et al., Molecular Cloning: A Laboratory Manual, Cold Spring Harbor Laboratory Press, Cold Spring Harbor, N.Y., 1989, Gait, M. J., ed., 1984; Nucleic Acid Hybridization, Hames, B. D., and Higgins, S. J., eds., 1984; and a series, Methods in Enzymology, Academic Press, Inc., all of which are incorporated herein by reference. All patents, patent applications, and publications mentioned herein, both supra and infra, are incorporated herein by reference. In an embodiment of the invention, a method is provided to avoid (or to inhibit or to prevent) the amplification of a non-methylated target nucleic acid by performing a restriction enzyme digest after the bisulfite treatment which digests non-methylated target nucleic acid after the bisulfite treatment of DNA that can lead to wrong results and can therefore be regarded as a contaminating nucleic acid or a contamination in general. Potential contaminations of the sample are ubiquitous, possible at any step of a method, difficult to avoid and can originate from diverse sources (see FIGS. 2 and 3 for an exemplary survey of the method). The bisulfite reaction is the step wherein non-methylated cytosine bases are converted to uracil bases whereas 5-methylcytosine bases are not converted.

Figure 1:
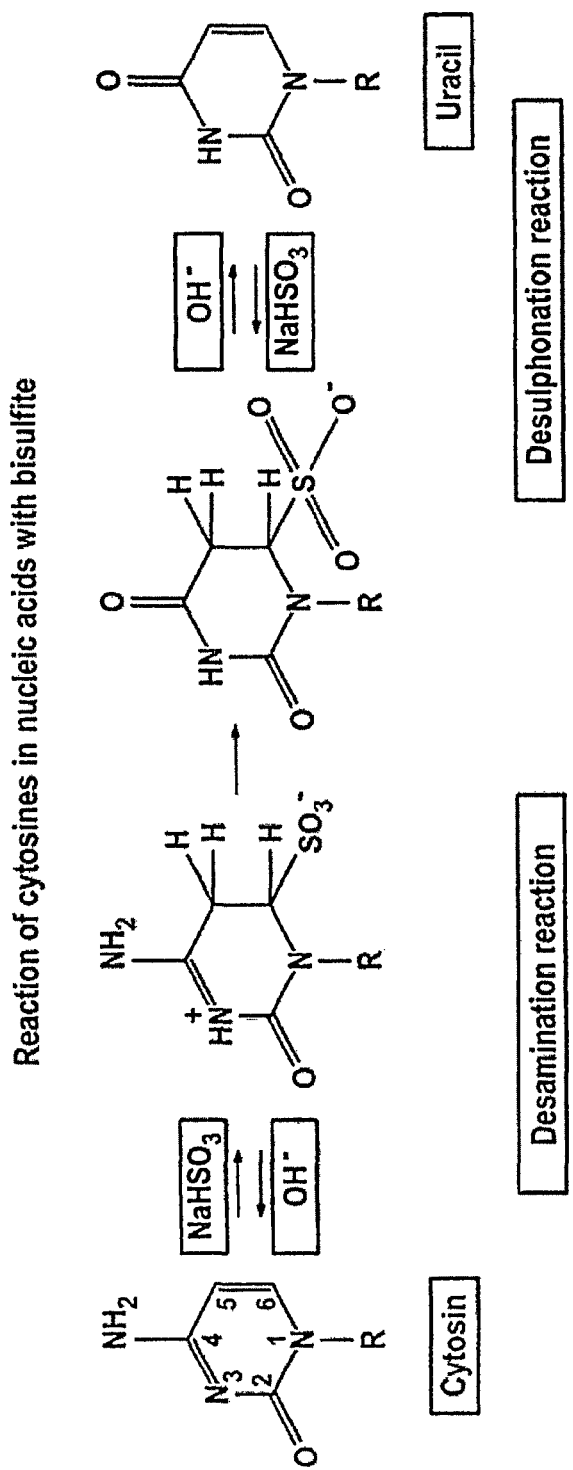
FIG. 1: The steps of the bisulfite method.
Figure 2:
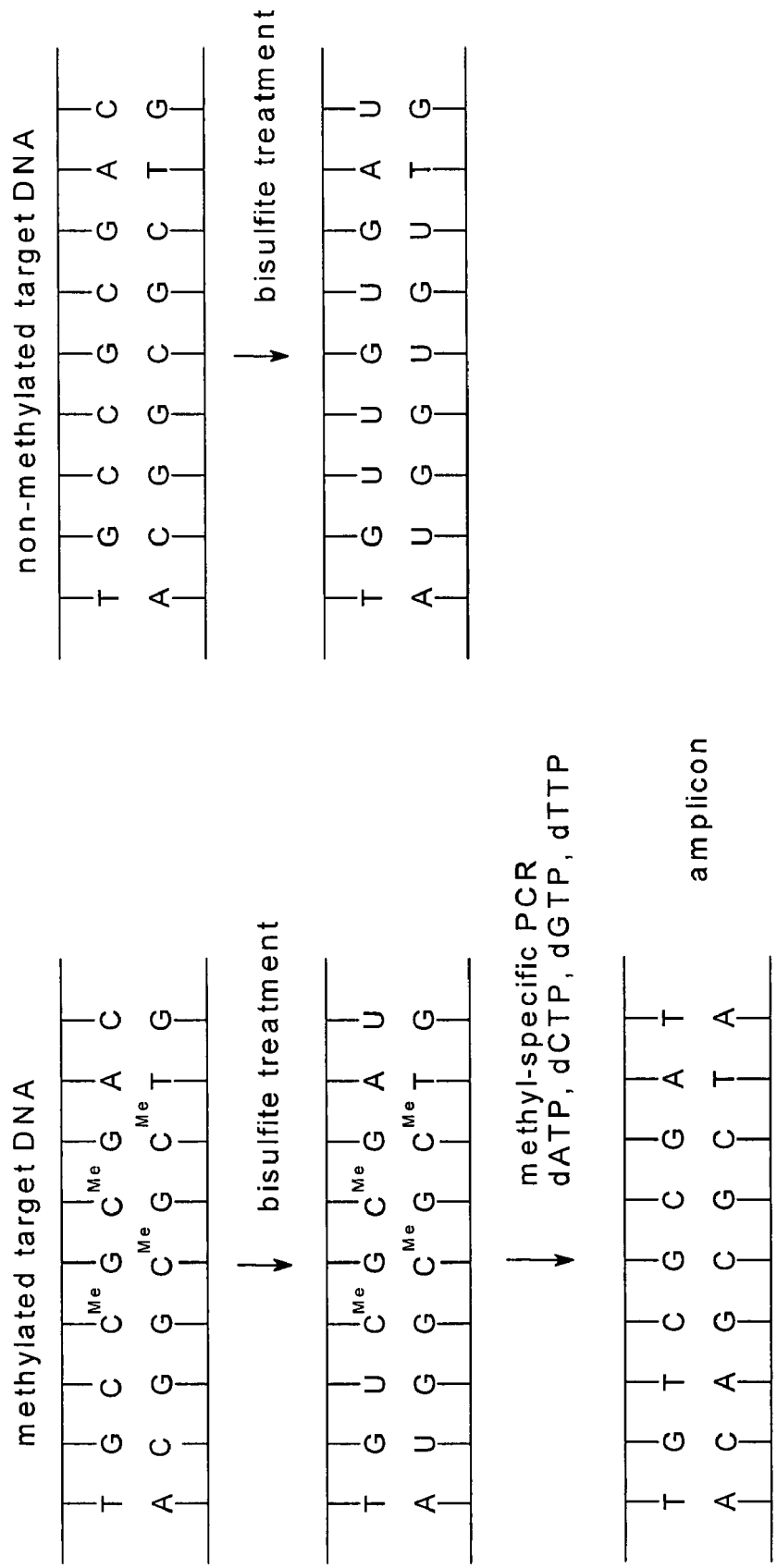
FIG. 2: An example of an amplification reaction after bisulfite treatment of a methylated and non-methylated target nucleic acid which may lead to amplified reaction products contaminating further amplification reactions as in FIG. 3.
Figure 3:
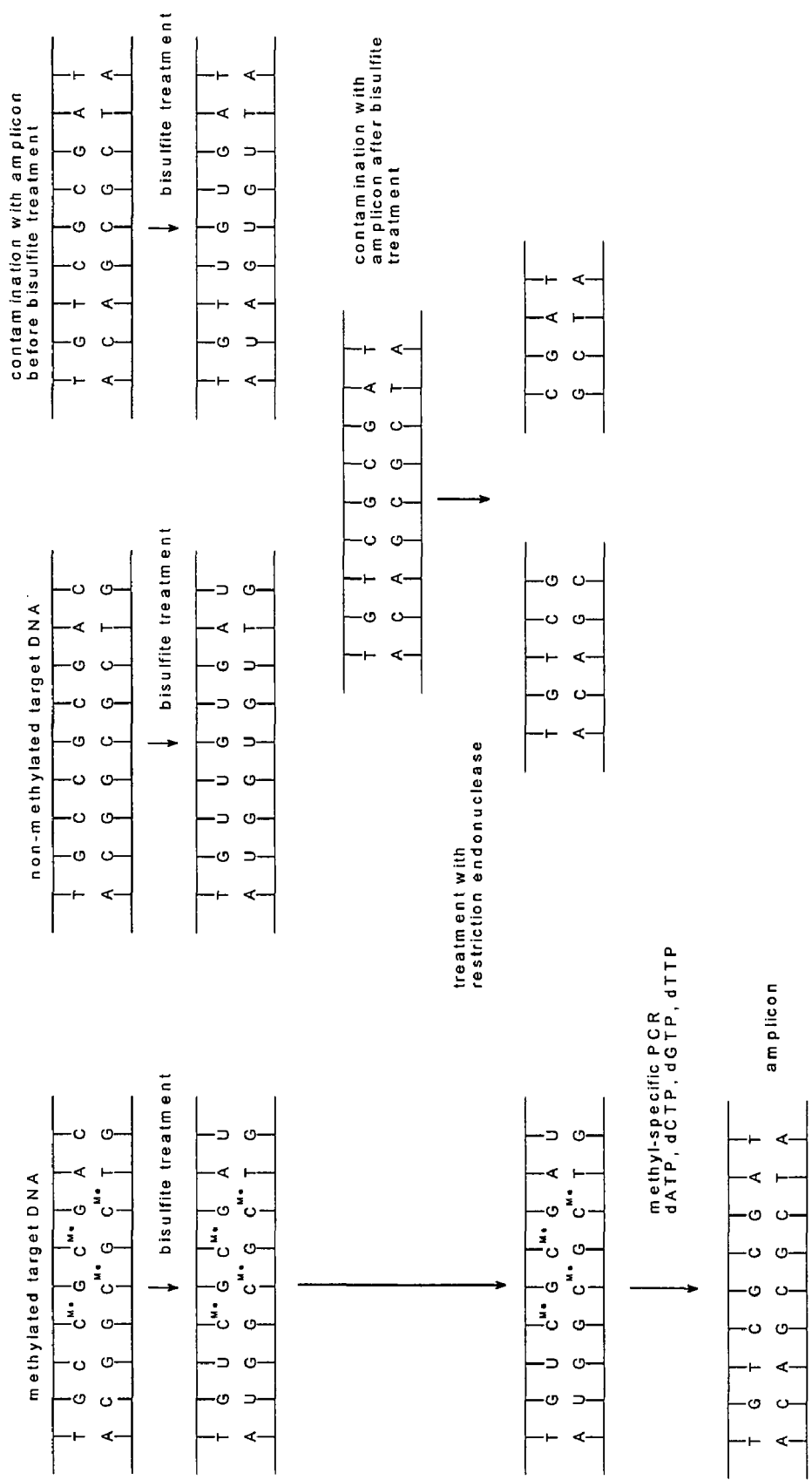
FIG. 3: An example of the decontamination of an amplification reaction after bisulfite treatment of a methylated and non-methylated target nucleic acid schematically showing bisulfite reaction products and the digestion thereof.

From FIGS. 2 and 3, it becomes apparent that a non-methylated target nucleic acid may be introduced before, after or during the bisulfite reaction. If the non-methylated target nucleic acid is present in the bisulfite step, a non-methylated cytosine base will be converted to an uracil base, the nucleic acid sequence will be changed and not be amenable to nucleic acid amplification or restriction digestion. In consequence, it will not disturb the amplification as the primers and probes are sequence-specific and are chosen by the person skilled in the art and not lead to false results, Hence the bisulfite reaction itself is already a decontamination of previously amplified target nucleic acids present during the bisulfite reaction when all non-methylated cytosine bases are converted to uracil bases. In consequence, the bisulfite step will generally convert a non-methylated cytosine base in the methylated target nucleic and in the non-methylated target nucleic acid in the sample into an uracil base while not converting a methyl-cytosine base or the methylcytosine base in the recognition nucleic acid sequence of the restriction enzyme wherein the recognition nucleic acid sequence is in the amplified reaction product.

The first source for the non-methylated target nucleic acid present after bisulfite treatment can be non-methylated target nucleic acid inadvertently introduced into the sample after the bisulfite treatment and stemming e.g. from previous (independent) amplifications reactions of the methylated target nucleic acid. This target nucleic acid does not comprise methylated cytosine bases as non-methylated cytosines are normally employed in amplification reactions producing non-methylated amplification reaction products or generally non-methylated target nucleic acids, i.e. non-methylated copies of the (originally) methylated target nucleic acid. The nucleic acid sequence of the non-methylated target nucleic acid, i.e. the amplification product of the methylated target nucleic acid, is identical to the methylated target nucleic acid and the said nucleic acid (molecule) only differs in its methylation of cytosine bases not affecting hydrogen bonding to complementary nucleic acids. The non-methylated target nucleic acid does not contain a nucleotide with a methyl-cytosine base in the recognition sequence of the restriction enzyme according to the invention.

A second possible source for "contaminating nucleic acid" or "non-methylated target nucleic acid" can be samples from other sources or more specifically human patients comprising such nucleic acid and being prepared in spatial proximity to the sample being analyzed.

The third source of "contaminating nucleic acid" or "non-methylated target nucleic acid" according to the invention can be "target nucleic acid" not fully converted in bisulfite treatment, i.e. it comprises a nucleotide with a cytosine base in the recognition nucleic acid sequence of a restriction enzyme, particularly the restriction enzyme chosen or used in step (b) of the method, but may contain a nucleotide with a methyl-cytosine base that is not in the recognition nucleic acid sequence of a restriction enzyme. According to the invention, this is also a "contaminating nucleic acid" although it is more generally a target nucleic acid comprising a methylcytosine base, but more specifically comprising a methylcytosine base that is not in the recognition nucleic acid sequence of a restriction enzyme used in step (b) of the method according to the invention and comprising a (non-methylated) cytosine base in the recognition nucleic acid sequence of a restriction enzyme used in step (b) of the method according to the invention. According to the invention, this is understood to be a non-methylated target nucleic acid.

The fourth source of contaminating nucleic acid can be non-methylated target nucleic acid from other previous (independent) amplification reactions of the methylated target nucleic acid that was present during the bisulfite treatment and that was not fully converted during bisulfite treatment, i.e. a non-methylated cytosine base in the recognition nucleic acid sequence of a restriction enzyme, particularly the restriction enzyme chosen or used in step (b) of the method, was not converted to an uracil base. In other words, it comprises after bisulfite treatment a nucleotide with a (non-methylated) cytosine base in the recognition nucleic acid sequence of a restriction enzyme, particularly the restriction enzyme chosen or used in step (b) of the method.

Therefore, it is an embodiment of the invention to provide a method for amplifying a methylated target nucleic acid in a sample while avoiding amplification of a non-methylated target nucleic acid whereby the methylated target nucleic acid comprises a nucleotide with a methylcytosine base in the recognition nucleic acid sequence of a restriction enzyme wherein the recognition nucleic acid sequence is in the amplified reaction product the method comprising, preferably in the following order, the steps of:
(a) converting a non-methylated cytosine base in the methylated target nucleic acid in the sample into an uracil base while not converting the methylcytosine base;
(b) adding a restriction enzyme to the sample which digests the non-methylated target nucleic acid whereby the methylated target nucleic acid is not digested by the restriction enzyme;
(c) inactivating the restriction enzyme; and
(d) amplifying the methylated target nucleic acid.

Preferably, the method according to the invention consists of the specified steps.

As said above, for example a previously amplified target nucleic acid not fully converted, i.e. containing cytosine bases not converted to uracil bases, may lead to false results as well as non-methylated target nucleic acid not present in the sample during the bisulfite step. These species shall then be digested by the restriction enzyme added, i.e. a restriction enzyme added to the sample digests the non-methylated target nucleic acid not present in the sample in step a) of the method according to the invention or the non-methylated target nucleic acid comprising a nucleotide with a cytosine base in the recognition nucleic acid sequence of the restriction enzyme which was not converted in step a) of the method according to the invention whereby the methylated target nucleic acid is not digested by the restriction enzyme.

Therefore, it is an embodiment of the invention to provide a method for amplifying a methylated target nucleic acid in a sample while avoiding amplification of a non-methylated target nucleic acid whereby the methylated target nucleic acid comprises a nucleotide with a methylcytosine base in the recognition nucleic acid sequence of a restriction enzyme wherein the recognition nucleic acid sequence is in the amplified reaction product the method comprising in the following order the steps of:
(a) converting a non-methylated cytosine base in the methylated target nucleic acid and in the non-methylated target nucleic acid in the sample into an uracil base while not converting the methylcytosine base;
(b) adding a restriction enzyme to the sample which digests the non-methylated target nucleic acid not present in the sample in step a) or
the non-methylated target nucleic acid comprising nucleotides or a nucleotide with a cytosine base in the recognition nucleic acid sequence of the restriction enzyme which was or were not converted in step a) whereby the methylated target nucleic acid is not digested by the restriction enzyme;
(c) inactivating the restriction enzyme; and
(d) amplifying the methylated target nucleic acid.

Preferably, the method according to the invention consists of the specified steps.

The non-methylated target nucleic acid is inadvertently or optionally present in or introduced into the sample, preferably before, during or after the bisulfite treatment, i.e. step a) of the method according to the invention, or before or during the restriction enzyme digest, i.e. step b) of the method according to the invention.

Therefore, in still another embodiment of the invention, a method is provided for amplifying a methylated target nucleic acid in a sample while avoiding amplification of a non-methylated target nucleic acid or contaminating nucleic acid, optionally present in or optionally introduced into the sample, the method comprising in the following order the steps of:
(a) converting a non-methylated cytosine base in the methylated target nucleic acid and in the non-methylated target nucleic acid in the sample into an uracil base while not converting the methylcytosine base;
(b) adding a restriction enzyme to the sample which digests the non-methylated target nucleic acid that is optionally present in the sample or optionally inadvertently introduced into the sample, whereby the methylated target nucleic acid is not digested by the restriction enzyme;
(c) inactivating the restriction enzyme; and
(d) amplifying the methylated target nucleic acid.

Preferably, the method according to the invention consists of the specified steps.

In the method according to the invention, the methylated target nucleic acid comprises a nucleotide with a methylcytosine base in the recognition nucleic acid sequence of a restriction enzyme wherein the recognition nucleic acid sequence is in the amplified reaction product. The non-methylated target nucleic acid comprises a nucleotide with a cytosine base in the recognition nucleic acid sequence of a restriction enzyme (wherein the recognition nucleic acid sequence is in the amplified reaction product).

The expert skilled in the art knows how to perform the bisulfite reaction, i.e. step a) of the method according to the invention, e.g. by referring to Frommer et al., supra or Grigg and Clark, supra who disclose the principal parameters of the bisulfite reaction. From Grunau et al., supra, it is known to the expert in the field what variations of the bisulfite method are possible. The influence of incubation time and temperature on deamination efficiency and parameters affecting DNA degradation is disclosed. In summary, in the deamination step a buffer containing bisulfite ions and optionally chaotropic agents as guanidinium ions or urea and further reagents as an alcohol or stabilizers as hydroquinone are employed and the pH is in the acidic range. The concentration of bisulfite is between 0.1 to 8 M bisulfite, preferably 0.1 to 6 M, more preferably 0.1 M to 5.5 M, the concentration of the chaotropic agent is between 1 to 8 M, whereby in general preferably guanidinium salts are employed, more preferably guanidinium hydrogen sulfite as described in EP 3027754.5, the pH is in the acidic range, preferably between 4.5 to 6.5, the temperature is between 0° C. to 90° C., preferably between room temperature (25° C.) to 90° C., and the reaction time is between 30 min to 24 hours or 48 hours or even longer, but preferably between 1 hour to 24 hours.

The desulfonation step is performed by adding an alkaline solution or buffer as e.g. a solution only containing a hydroxide, e.g. sodium hydroxide, or a solution containing ethanol, sodium chloride and sodium hydroxide (e.g. 38% EtOH, 100 mM NaCl, 200 mM NaOH) and incubating at room temperature or elevated temperatures for several min, preferably 5 min to 60 min. Desalting of the nucleic acid can be performed using magnetic glass particles as described in WO 96/41811, specifically described for the bisulfite reaction in EP 1 394 173. It is also possible to use a kit commercially available from Intergen, distributed by Serologicals Corporation, Norcross, Ga., USA, e.g. CpGenome™ DNA modification kit.

Therefore, in a preferred embodiment of the invention, a method is provided wherein in step a) of the method the presence of sulfite ions in the sample converts the non-methylated cytosine base in the methylated target nucleic acid in the sample into the uracil base. More preferably, the method comprises in step a) the substeps of a1) mixing the sample comprising the methylated target nucleic acid with a solution comprising sulfite ions; a2) incubating the solution obtained in step a1) comprising the methylated target nucleic acid and sulfite ions whereby the target nucleic acid is deaminated, a3) incubating the deaminated nucleic acid under alkaline conditions whereby the deaminated nucleic acid is desulfonated, and a4) desalting the deaminated nucleic acid. The concentration of sulfite ions is preferably 0.1 to 8 M, more preferably 0.1 to 6.25 M, 0.1 to 6 M, more preferably 2 to 6 M. The pH of the solutions in step a1) and a2) is preferably in the acidic range, more preferably between 4.5 to 6.5. The incubation temperature in step a2) and a3) is preferably between 0° C. to 90° C., preferably between 18° C. to 90° C. The incubation time in step a2) is preferably between 30 min to 48 hours, more preferably 24 hours. Preferably the step a3) is performed by adding an alkaline solution or buffer, more preferably a solution containing a hydroxide, most preferably sodium hydroxide, or a solution containing ethanol, sodium chloride and sodium hydroxide, most preferred is a solution containing 38% (volume/volume) ethanol, 100 mM NaCl, 200 mM NaOH. The incubation time in step a3) is preferably between 5 min to 60 min.

In a preferred embodiment of the invention, the incubation parameters as described in WO 2004/067545 may be used, wherein the nucleic acid is incubated in a solution for a time period of 1.5 to 3.5 hours at a temperature between 70 and 90° C., whereby the concentration of bisulfite in the solution is between 3 M and 6.25 M and whereby the pH value of the solution is between 5.0 and 6.0 whereby the nucleic acid is deaminated.

In another preferred embodiment the bisulfite reaction is bound to a solid phase bound DNA as disclosed in EP 1 394 173, preferably the solid phase is a solid phase comprising glass, more preferably a glass fiber or a magnetic glass particle (MGP). Therefore, in a preferred embodiment of the invention the deamination step a2), desulfonation step a3) and/or desalting step a4) is performed while the target nucleic acid is bound to a solid phase comprising a glass surface.

In an embodiment of the invention, the methylated target nucleic acid is deoxyribonucleic acid (DNA), in particular genomic DNA, i.e. the DNA or nucleic acid which is found in the organism's genome and is passed on to offspring as information necessary for survival. The phrase is used to distinguish between other types of DNA, such as found within plasmids. The source of the nucleic acid may be eukaryotic or prokaryotic, preferably from vertebrates, particularly from mammalians, most preferred from animals or humans.

In an embodiment of the invention the nucleic acid is obtained from a biological sample using, e.g. solid phases (see e.g. WO 96/41811 or WO 01/37291 or the MagNAPure® System available from Roche Diagnostics, Mannheim Germany) or other methods known to the expert in the field (see e.g. Sambrook, J., et al., In: Molecular Cloning, A Laboratory Manual, 2nd ed., Cold Spring Harbor Laboratory Press, Cold Spring Harbor, N.Y.; and Ausubel et al., In: Current Protocols in Molecular Biology, 1987, J. Wiley and Sons, NY, or commercial DNA isolation kits available e.g. from Qiagen, Hilden Germany). The biological sample comprises cells from multicellular organisms as e.g. human and animal cells such as leucocytes, and immunologically active low and high molecular chemical compounds such as haptens, antigens, antibodies and nucleic acids, blood plasma, cerebral fluid, sputum, stool, biopsy specimens, bone marrow, oral rinses, blood serum, tissues, urine or mixtures thereof. In a preferred embodiment of the invention the biological sample is a fluid from the human or animal body. The biological sample may be blood, blood plasma, blood serum or urine. The biological sample comprising the nucleic acid is lysed to create a mixture of biological compounds comprising nucleic acids and other components. Procedures for lysing biological samples are known by the expert and can be chemical, enzymatic or physical in nature. A combination of these procedures is applicable as well. For instance, lysis can be performed using ultrasound, high pressure, shear forces, alkali, detergents or chaotropic saline solutions, or proteases or lipases. For the lysis procedure to obtain nucleic acids, special reference is made to Sambrook, J., et al., In: Molecular Cloning, A Laboratory Manual, 2nd ed., Cold Spring Harbor Laboratory Press, Cold Spring Harbor, N.Y.; and Ausubel et al., In: Current Protocols in Molecular Biology, 1987, J. Wiley and Sons, NY. Then the nucleic acids are isolated from the lysis mixture using the described methods and solid phases and can then be subjected to the bisulfite treatment. Chaotropic agents are also used to lyse cells to prepare a mixture between nucleic acids and other biological substances (see e.g. Sambrook, J., et al. (1989) or EP 0 389 063). Afterwards the material comprising glass or silica may be added and a purification effect results from the behavior of DNA or RNA to bind to material with a glass surface under these conditions i.e. in the presence of certain concentrations of a chaotropic agent, higher concentrations of organic solvents or under acidic conditions. Alternative methods may be used as well.

The restriction enzyme digestion step is performed preferably as described by e.g. Sambrook, J., et al., In: Molecular Cloning: A Laboratory Manual, Cold Spring Harbor Laboratory Press, Cold Spring Harbor, N.Y. (1989) or according to the description of the manufacturer which may be e.g. New England Biolabs, Beverly, Mass., USA, Fermentas, Vilnius, Lithuania or Roche Diagnostics GmbH, Mannheim Germany. In more detail, the conditions may be between room temperature (25° C.) up to 65° C. for thermostable enzymes, preferably at about 37° C. for about 5 min to 24 hours, preferably 5 min to 6 hours, more preferably 2 to 4 hours under the salt conditions and enzyme concentrations according to the manufacturer. For analytical purposes, typically 1 microgram of DNA fragment is used with about 2 units of enzyme in about 20 microliter of buffer solution. For the purpose of isolating DNA fragments for other purposes, typically 5 to 50 microgram of DNA are digested with 20 to 250 units of enzyme in a larger volume. Most preferred is that the incubation time and conditions as salt conditions, enzyme concentrations and DNA amount are used according to recommendations of the manufacturer.

In an embodiment of the invention, the restriction enzyme is preferably a methylation-sensitive restriction enzyme, i.e. the cleavage or digest of a nucleic acid by the restriction enzyme is (preferably totally) blocked or inhibited by partial or total methylation, preferably at all sites, or in other words by the presence of a nucleotide comprising a 5-methyl-cytosine base within the recognition nucleic acid sequence of the restriction enzyme. In still other words, a dinucleotide CpG is part of or contained within the recognition nucleic acid sequence of the restriction enzyme and the presence of a nucleotide comprising a 5-methyl-cytosine base in the dinucleotide CpG within the recognition nucleic acid sequence of the restriction enzyme leads to a block or inhibition, preferably total block or inhibition, of the activity of the restriction enzyme to cleave or digest a nucleic acid or a dinucleotide CpG is part of or contained within the recognition nucleic acid sequence of the restriction enzyme and the presence of a nucleotide comprising a 5-methyl-cytosine base in the dinucleotide CpG within the recognition nucleic acid sequence of the restriction enzyme blocks or inhibits, preferably totally, the cleavage or digest of a nucleic acid by the restriction enzyme.

Preferably, the nucleotide with a methylcytosine base in the recognition nucleic acid sequence is flanked at the 3' side by a nucleotide with a guanine base whereby the nucleotide with a guanine base is part of the recognition nucleic acid sequence, i.e. the dinucleotide CpG is located or contained within the recognition nucleic acid sequence of the restriction enzyme. Therefore, the restriction enzyme is preferably selected from the group consisting of the restriction enzymes Acl I, BsiW I, BspD I, Bst BI, BstU I, Cla I, HpyCH4 IV, Mlu I, Nru I, Pvu I, and SnaB I. Alternatively, also the isoschizomers of the restriction enzymes mentioned-above may be used. Then, the restriction enzyme is preferably selected from the group consisting of the restriction enzymes Acl I, BsiW I, BspD I, Bst BI, BstU I, Cla I, HpyCH4 IV, Mlu I, Nru I, Pvu I, SnaB I and an isoschizomer thereof.

In another preferred embodiment, the nucleotide with a methylcytosine base in the recognition nucleic acid sequence of the restriction enzyme is flanked at the 3' side by a nucleotide with a guanine base, whereby the nucleotide with a guanine base is not part of or contained within the recognition nucleic acid sequence of the restriction enzyme (but directly adjacent thereto). Therefore, in another embodiment cleavage of a nucleic acid by the restriction enzyme is blocked or impaired only at sites with CG dinucleotides overlapping with the recognition nucleic acid sequence of the restriction enzyme. Therefore, it is selected from the group consisting of the restriction enzymes BsmF I, BstZ I, Dpn II, Eci I, EcoR I, EcoR V, Hpa I, Mbo I, Ple I, Pme I, Rsa I, Sal I, and Sau3A I. Alternatively, also the isoschizomers of the restriction enzymes mentioned-above may be used. Then, the restriction enzyme is preferably selected from the group consisting of the restriction enzymes BsmF I, BstZ I, Dpn II, Eci I, EcoR I, EcoR V, Hpa I, Mbo I, Ple I, Pme I, Rsa I, Sal I, Sau3A I and an isoschizomer thereof.

In a preferred embodiment of the invention, the restriction enzyme is thermally inactivated in step c) of the method according to the invention, i.e. the temperature is raised and the restriction enzyme is inactivated by thermal denaturation of the restriction enzyme. The inactivating step c) and the amplifying step d) in the method according to the invention are preferably carried out in the same step.

In the method according to the invention, the amplification reagents for use in the amplifying step d) and the restriction enzyme are combined with the sample before the amplifying step d). This can be done separately or in combination. Therefore, in a preferred embodiment of the invention, the amplification reagents for use in said amplifying step d) and the restriction enzyme are combined as a mixture with the sample. The amplification reagents comprise nucleotides, a pair of primers, an oligonucleotide, a probe or a DNA polymerase. It may also contain other oligonucleotides which may be labeled. The probe can be labeled, in particular in a way that it can be easily used in the formats applied in the TaqMan® (WO 92/02638 and the corresponding U.S. Pat. No. 5,210,015, U.S. Pat. No. 5,804,375, U.S. Pat. No. 5,487,972) or the LightCycler® instrument (see e.g. U.S. Pat. No. 6,174,670).

In a preferred embodiment of the invention, the nucleic acid is amplified with the polymerase chain reaction (PCR; EP 0 201 184, EP-A-0 200 362, U.S. Pat. No. 4,683,202). The amplification method may also be the Ligase Chain Reaction (LCR, Wu, D. Y., and Wallace, R. B., Genomics 4 (1989) 560-569 and Barany, F., Proc. Natl. Acad. Sci. USA 88 (1991) 189-193; Polymerase Ligase Chain Reaction (Barany, F., PCR Methods Appl. 1 (1991) 5-16); Gap-LCR (PCT Patent Publication No. WO 90/01069); Repair Chain Reaction (European Patent Publication No. EP 439,182 A2), 3SR (Kwoh, D. Y., et al., Proc. Natl. Acad. Sci. USA 86 (1989) 1173-1177; Guatelli, J. C., et al., Proc. Natl. Acad. Sci. USA 87 (1990) 1874-1878; PCT Patent Publication No. WO 92/0880A), and NASBA (U.S. Pat. No. 5,130,238). Further, there are strand displacement amplification (SDA), transcription mediated amplification (TMA), and Qβ-amplification (for a review see e.g. Whelen, A. C., and Persing, D. H., Annu. Rev. Microbiol. 50 (1996) 349-373; Abramson, R. D., and Myers, T. W., Curr. Opin. Biotechnol. 4 (1993) 41-47). Particularly preferred amplification methods according to the invention are the methylation specific PCR method (MSP) disclosed in U.S. Pat. No. 5,786,146 which combines bisulfite treatment and allele-specific PCR (see e.g. U.S. Pat. No. 5,137,806, U.S. Pat. No. 5,595,890, U.S. Pat. No. 5,639,611) or the combination of blocking probes with primers in PCR reactions (WO2002/072880).

In a preferred embodiment, the method may further comprise the step of detecting the amplified nucleic acid. The amplified nucleic acid may be determined or detected by standard analytical methods known to the person skilled in the art and described e.g. in Sambrook, J. et al., Molecular Cloning, Cold Spring Harbor University Press (1989), Lottspeich and Zorbas, in "Bioanalytik" (1998), Eds. L. a. Zorbas, Spektrum Akademischer Verlag, Heidelberg, Berlin, Germany, or in Ausubel, F., et al., in "Current protocols in molecular biology" (1994), Eds. F. Ausubel, R. Brent and K. R. E., Wiley & Sons Verlag, New York. There may be also further purification steps before the target nucleic acid is detected e.g. a precipitation step. The detection methods may include but are not limited to the binding or intercalating of specific dyes as ethidium bromide which intercalates into the double-stranded DNA and changes its fluorescence thereafter. The purified nucleic acids may also be separated by electrophoretic methods optionally after a restriction digest and visualized thereafter. There are also probe-based assays which exploit the oligonucleotide hybridization to specific sequences and subsequent detection of the hybrid. It is also possible to sequence the target nucleic acid after further steps known to the expert in the field. Other methods apply a diversity of nucleic acid sequences to a silicon chip to which specific probes are bound and yield a signal when a complementary sequences bind.

In a particularly preferred embodiment of the invention, the nucleic acid is detected by measuring the intensity of fluorescence light during amplification. This method entails the monitoring of real time fluorescence. A particularly preferred method exploiting simultaneous amplification and detection by measuring the intensity of fluorescent light is the TaqMan® method disclosed in WO 92/02638 and the corresponding U.S. Pat. No. 5,210,015, U.S. Pat. No. 5,804,375, U.S. Pat. No. 5,487,972. This method exploits the exonuclease activity of a polymerase to generate a signal. In detail, the nucleic acid is detected by a process comprising contacting the sample with an oligonucleotide containing a sequence complementary to a region of the target nucleic acid and a labeled oligonucleotide containing a sequence complementary to a second region of the same target nucleic acid strand, but not including the nucleic acid sequence defined by the first oligonucleotide, to create a mixture of duplexes during hybridization conditions, wherein the duplexes comprise the target nucleic acid annealed to the first oligonucleotide and to the labeled oligonucleotide such that the 3'-end of the first oligonucleotide is adjacent to the 5'-end of the labeled oligonucleotide. Then this mixture is treated with a template-dependent nucleic acid polymerase having a 5' to 3' nuclease activity under conditions sufficient to permit the 5' to 3' nuclease activity of the polymerase to cleave the annealed, labeled oligonucleotide and release labeled fragments. The signal generated by the hydrolysis of the labeled oligonucleotide is detected and/or measured. TaqMan® technology eliminates the need for a solid phase bound reaction complex to be formed and made detectable. In more general terms, the amplification and/or detection reaction of the method according to the invention is a homogeneous solution-phase assay. Further preferred method are the formats used in the LightCyclere instrument (see e.g. U.S. Pat. No. 6,174,670). Particularly preferred is the use of bisulfite treatment, amplification with or without methylation specific primers in the presence of a methylation-specific probe and real-time fluorescence detection as described in U.S. Pat. No. 6,331,393.

Therefore, in a preferred embodiment of the invention, a method according to the invention is provided further comprising, after the amplifying step d) or concurrently with the amplifying step d), detecting any amplification product produced in said amplifying step as an indication of the presence or the amount of the target nucleic acid in the sample.

In a preferred embodiment of the present invention, the method is automated, i.e. the method carries out an automatable process as e.g. described in WO 99/16781. Automatable process means that the steps of the process are suitable to be carried out with an apparatus or machine capable of operating with little or no external control or influence by a human being. Automated method means that the steps of the automatable method are carried out with an apparatus or machine capable of operating with little or no external control or influence by a human being. Only the preparation steps for the method may have to be done by hand, e.g. the storage containers have to filled up and put into place, the choice of the samples has to be done by a human being and further steps known to the expert in the field, e.g. the operation of the controlling computer. The apparatus or machine may e.g. add automatically liquids, mix the samples or carry out incubation steps at specific temperatures. Typically, such a machine or apparatus is a robot controlled by a computer which carries out a program in which the single steps and commands are specified. In a preferred embodiment of the invention, the method is in a high-throughput format, i.e. the automated methods is carried out in a high-throughput format which means that the methods and the used machine or apparatus are optimized for a high-throughput of samples in a short time.

Preferably the method according to the invention is used in diagnostics, for diagnostic analysis or for bioanalytics, or for the screening of tissue or fluids from the human or even animal body for the presence of certain methylation pattern. Further, the method according to the invention is used to enhance the speed, accuracy or sensitivity of the detection of methylation sites in nucleic acids.

It is a preferred embodiment of the invention to provide a method for controlling contamination in sequential target nucleic acid amplification processes comprising a first and a second nucleic acid amplification process to amplify a target nucleic acid in a first and second sample, respectively, which comprises carrying out the first nucleic acid amplification process on the target nucleic acid sequence in the first sample prior to carrying out the second amplification process on the target nucleic acid in the second sample according to the invention.

In another embodiment of the invention, a restriction enzyme is used to digest non-methylated target nucleic acid in a sample comprising a methylated target nucleic acid whereby the non-methylated target nucleic acid was not present in the sample during the conversion of a non-methylated cytosine base in the methylated target nucleic acid into an uracil base while not converting the methylcytosine. The restriction enzyme is preferably a methylation-sensitive restriction enzyme, preferably selected from the groups described above.

Such kits known in the art further comprise plastics ware which can be used during the amplification procedure as e.g. microtitre plates in the 96 or 384 well format or just ordinary reaction tubes manufactured e.g. by Eppendorf, Hamburg, Germany and all other reagents for carrying out the method according to the invention.

In another preferred embodiment, a kit of parts is provided comprising a restriction enzyme, a compound comprising sulfite ions and a solid phase comprising a glass surface.

In another embodiment a kit is provided comprising a restriction enzyme, a compound comprising sulfite ions, a solid phase comprising a glass surface, a pair of primers, a probe and a DNA polymerase, preferably a thermostable DNA polymerase as e.g. Taq polymerase. The compound comprising bisulfite ions is e.g. sodium bisulfite or other alkaline bisulfates. The restriction enzyme is preferably a methylation-sensitive restriction enzyme, preferably selected from the groups described above. The kits according to the invention may also contain another oligonucleotide which may be used according to the method described in WO2002/072880. The probe according to the invention may optionally be labeled with dyes known to the expert skilled in the art.

In another embodiment of the invention, the kit contains reagents for isolating the nucleic acid which may also be used for performing the bisulfite reaction on a solid phase as described supra. Therefore, the kit may contain a material with an affinity to nucleic acids, preferably the material with an affinity to nucleic acids comprises a material with a silica surface. Preferably, the material with a silica surface is a glass. Most preferably, the material with an affinity to nucleic acids is a composition comprising magnetic glass particles as described in WO 96/41811 or WO 01/37291. The kit can further or additionally comprise a lysis buffer containing e.g. chaotropic agents, detergents or alcohols or mixtures thereof which allows the lysis of cells and separately a protease, e.g. proteinase K, for the digestions of unwanted proteins. These components of the kit according to the invention may be provided separately in tubes or storage containers. Depending on the nature of the components, these may be even provided in a single tube or storage container. The kit may further or additionally comprise a washing solution which is suitable for the washing step of the magnetic glass particles when DNA or RNA is bound thereto. This washing solution may contain ethanol and/or chaotropic agents in a buffered solution or solutions with an acidic pH without ethanol and/or chaotropic agents as described above. Often the washing solution or other solutions are provided as stock solutions which have to be diluted before use. The kit may further or additionally comprise an eluent or elution buffer, i.e. a solution or a buffer (e.g. 10 mM Tris, 1 mM EDTA, pH 8.0) or pure water to elute the DNA or RNA bound to the magnetic glass particles. Further, additional reagents or buffered solutions may be present which can be used for the purification process of a nucleic acid, i.e. DNA or RNA.

The following examples, references, sequence listing and figures are provided to aid the understanding of the present invention, the true scope of which is set forth in the appended claims. It is understood that modifications can be made in the procedures set forth without departing from the spirit of the invention.

EXAMPLES

Example 1

Decontamination of Amplicons by Restriction Enzyme Digest

Background:

The fact that the bisulfite reaction has worked and converted non-methylated cytosines to uracil can be demonstrated by a polymerase chain reaction whereby primers are used which are specific to a region of the nucleic acid sequence wherein non-methylated cytosines have been converted to uracils, i.e. the base adenine in the primer is opposite to the uracil being the bisulfite reaction product from non-methylated cytosines. In case of incomplete conversion, the primer could not hybridize to this region as there would be cytosines not matching the adenine bases in the primer. This would have the effect that no PCR product would be obtained.

An improved method to perform rapid polymerase chain reactions is disclosed e.g. in U.S. Pat. No. 6,174,670 and is used in the LightCycler® instrument (Roche, Mannheim, Germany). In this method, two labeled probes can come into close proximity in an amplificate dependent manner so that the two labels can perform a fluorescence energy transfer (FRET). The amount of the amplificate thereby correlates with the intensity of the emitted light of a certain wavelength. This specific PCR method can therefore be used to analyze whether a complete conversion of non-methylated cytosines was obtained using suitable probes and primers. However, the expert skilled in the art knows that other methods can be used for this evaluation as well. Fluorescence measurements are normalized by dividing by an initial fluorescence measurement, i.e., the background fluorescence, obtained during a cycle early in the reaction while the fluorescence measurements between cycles appear to be relatively constant. The cycle number chosen for the initial fluorescence measurement is the same for all reactions compared, so that all measurements represent increases relative to the same reaction cycle. In the early cycles of a polymerase chain reaction amplification, the number of target molecules can be described by the geometric equation $N_i = N_o \times (1+E)^i$, where $N_o$=the number of target molecules at the start of the reaction, $N_i$=the number of target molecules at the completion of the i-th cycle, E=the efficiency of the amplification ($0 =< E =< 1$). During this geometric growth phase of the amplification, the number of cycles required to reach a particular threshold value ($C_T$ or $C_P$ value or crossing point) is inversely proportional to the logarithm of (1+E). Thus, the $C_T$ or $C_P$ value represents a measure of the reaction efficiency that allows comparisons between reactions.

A decrease in the $C_T$ or $C_P$ value, which means that the reaction reached the threshold value in fewer cycles, indicates an increase in reaction efficiency. As the increase in amplification product is monitored by measuring the increase in reaction fluorescence, the $C_T$ or $C_P$ is defined herein as the number of amplification cycles carried out until the fluorescence exceeded an arbitrary fluorescence level (AFL). The AFL was chosen close to the baseline fluorescence level, but above the range of random fluctuations in the measured fluorescence, so that the reaction kinetics were measured during the geometric growth phase of the amplification. Accumulation of amplified product in later cycles inhibits the reaction and eventually leads to a reaction plateau. An AFL of 1.5 was chosen for all reactions. Because a PCR amplification consists of discrete cycles and the fluorescence measurements are carried out once per cycle, the measured fluorescence typically increases from below the AFL to above the AFL in a single cycle. To improve the precision of the measurements, an "exact" number of cycles to reach the AFL threshold, referred to herein as the $C_T$ or $C_P$ value or crossing point, was calculated by interpolating fluorescence measurements between cycles.

DETAILED DESCRIPTION

Purified Amplicon-DNA was digested with a mix of the methylation specific restriction enzymes. After purification with the HIGH PURE PCR product purification kit, Roche Diagnostics GmbH, Mannheim, Germany, 10 µl of digested DNA was re-amplified in a real time kinetic PCR on the LightCycler® instrument, Roche Diagnostics GmbH, Mannheim, Germany according to the specifications of the manufacturer. DNA that was not digested but processed alike was used as a control.

Generation of purified Amplicon-DNA:

Methylated human genomic DNA (CpGENOME™ UNIVERSAL METHYLATED DNA from Serologicals Corporation, Norcross, Ga., USA) was bisulfite treated (e.g. using the EZ DNA Methylation™ Kit from Zymo Research, Orange, Calif., USA) and amplified using the LightCycler® FastStart DNA Master Hybridization Probes Kit (Roche Diagnostics GmbH, Mannheim, Germany). The following primer/probe set was used on the LightCycler® instrument (Roche Diagnostics GmbH, Mannheim, Germany):

```
Forward Primer (SEQ ID NO: 1):
5-TGC GGT CGA CGT T-3

Reverse Primer (SEQ ID NO: 2):
5-GCC GAC CGC TCT T-3

Hybprobe 1a (SEQ ID NO: 3):
5-CGG TCG TCG GGG TTG GG-Fluo-3

Fluo: Fluorescein label
HybProbe 1b (SEQ ID NO: 4):
5-LCRed-640-CGG CGG GAG TTC GCG G-Pho-3

Pho: 3'-phosphorylation;
LC-Red 640 (see EP 0 567 622 or US 5,750,409)
```

The Mastermix composition was as follows:

| Reagent | Final conc. | Microliter/PCR |
|---|---|---|
| PCR Water | | |
| Master Mix (1a (LightCycler Fast Start Enzyme) + 1b (LightCycler FastStart Reaction Mix Hybridization Probe) from the LightCycler ® FastStart DNA Master Hybridization Probes Kit) | 1x | |
| MgCl₂ | 2 mM | |
| Forward Primer (SEQ ID NO: 1) | 400 nM | |
| Reverse Primer (SEQ ID NO: 2) | 400 nM | |
| HybProbe 1a (SEQ ID NO: 3) | 200 nM | |
| HybProbe 1b (SEQ ID NO: 4) | 200 nM | |
| Sum | | 10.0 |
| Template | | 10.0 |

PCR-Profile Used:

| | | |
|---|---|---|
| Denaturation | 95° C. | 10 Min |
| Amplification | 95° C. | 10 sec |
| 50 Cycles | 58° C. | 10 sec |
| | 72° C. | 10 sec |
| Cooling | 40° C. | 30 sec |

The sequence of the amplicon (Methylated human genomic DNA from the CpGENOME™ UNIVERSAL METHYLATED DNA kit from Serologicals Corporation, Norcross, Ga., USA) is as follows, the CpG sites that are methylated before PCR in the bisulfite treated target, but no longer in the amplicon are shown in capital letters the rest in lower case letters; the recognition sites of the enzymes used are underlined:

(SEQ ID NO: 5)
5'-tgCGgtCGaCGttCGgggtgtagCGgtCGtCGgggttggggtCGgCG ggag-ttCGCGggattttttagaagagCGgtCGgC-3'

The resulting amplicon-DNA was diluted 1:10$^6$ in 10 mM Tris pH 8.0 and 20 µg/ml poly (dA) as stabilizing reagent, aliquoted and stored at −20° C. for further experiments.
Restriction Digest of Amplicon—DNA:

To 30 µl of the Amplicon-dilution from above 1 µl of the restriction enzymes HpyCH04 IV (recognition site A/CGT) and BstU1 (restriction site CG/CG) (both enzymes from New England Biolabs, Beverly, Mass., USA) was added as well as 5 µl of the 10× incubation buffer 1; water was added ad 50 µl. The mixture was incubated at 37° C. for 1 h followed by another 1 h incubation at 60° C. in a Thermomixer. After incubation the mixture was purified using the HIGH PURE PCR Product Purification Kit (Roche Diagnostics, Mannheim, Germany), elution volume was 40 µl.
Re-Amplification of Digested Amplicon-DNA:

10 µl of the purified digested Amplicon-DNA were re-amplified using the same PCR as described above under "Generation of purified Amplicon-DNA". As control a parallel sample was used where only the restriction enzyme was omitted (triplicates each)
Result:

| Sample | Cp-value 1 | Cp-value 2 | Cp-value 3 |
|---|---|---|---|
| Undigested Amplicon-DNA | 25.27 | 25.28 | 26.79 |
| Digested Amplicon-DNA | 35.84 | No growth curve | 36.05 |

Figure 4:
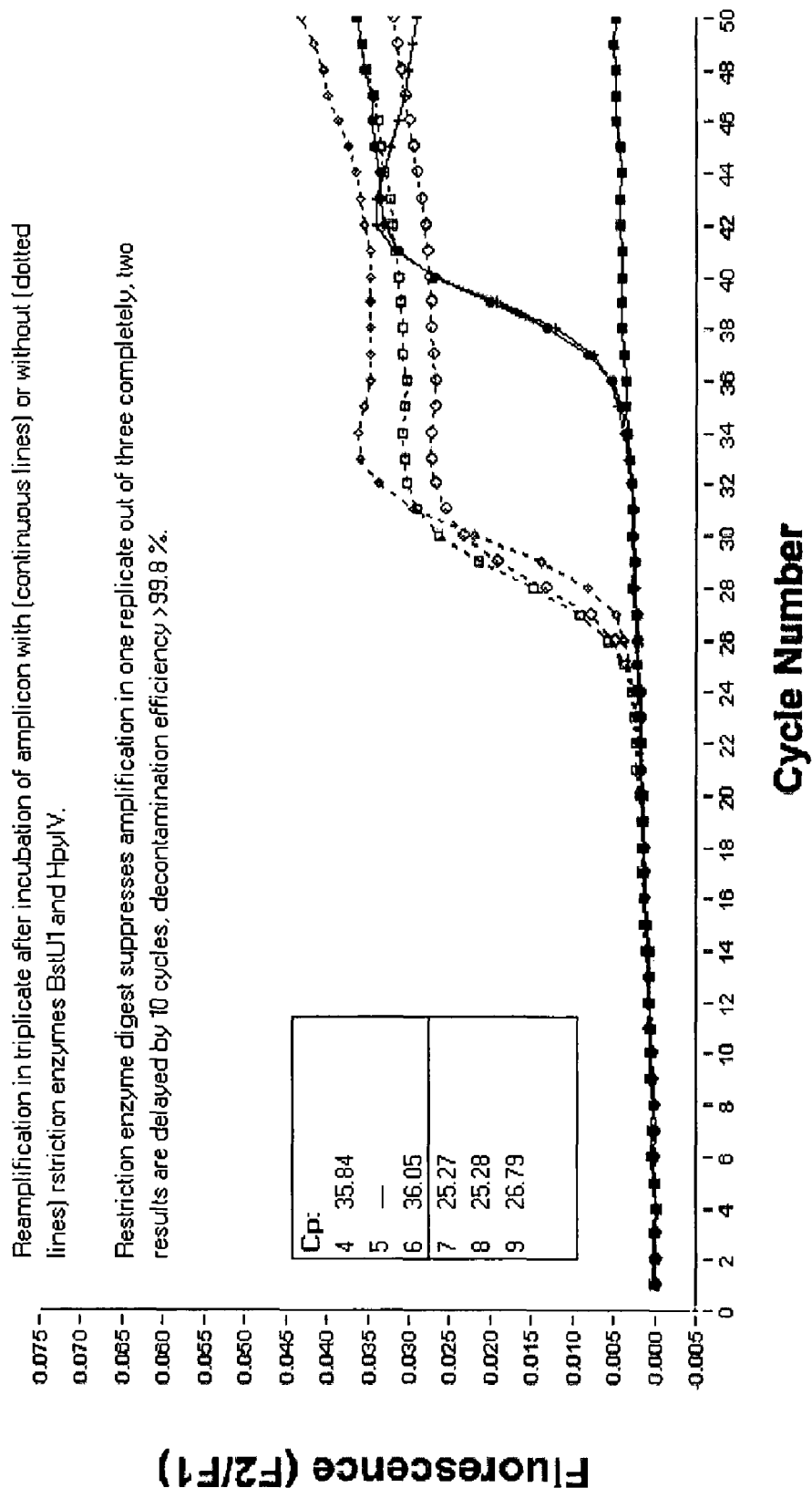
FIG. 4: Signal growth curves for the example "Re-amplification of digested Amplicon-DNA"

The growth curves are shown in FIG. 4.

The shift of the cp-value of about 10 from undigested to digested DNA shows that more than 99% of the unmethylated amplicon-DNA was digested by the restriction enzymes.

Example 2

Specificity of Restriction Enzyme Digest

Experimental Design:

Methylated DNA was digested with BstU1 and amplified as described above; undigested methylated DNA was used as control.
Result:

| Sample | Cp-value 1 | Cp-value 2 |
|---|---|---|
| Undigested DNA | 35.6 | 34.9 |
| Digested DNA | 34.2 | 35.4 |

The mean value of cp values of digested and undigested methylated DNA is comparable; this shows that methylated DNA is uninfluenced by restriction digest.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

The invention claimed is:

1. A method for amplification of a sample comprising a methylated target nucleic acid, and decontamination of the sample by removal of non-methylated contaminant target nucleic acid, the method consisting of the following steps in the sequence set forth:
   (a) performing a bisulfite reaction on the sample, thereby converting a non-methylated cytosine base into a uracil base while not converting a methylcytosine base, wherein the methylated target nucleic acid comprises at least one nucleotide with a methylcytosine base in a recognition nucleic acid sequence of a restriction enzyme;
   (b) adding a methylation-sensitive restriction enzyme to the sample which digests the non-methylated contaminant target nucleic acid, whereby after digestion the non-methylated contaminant target nucleic acid is no longer able to be amplified and the sample is decontaminated, whereby the methylated target nucleic acid is not digested by the methylation-sensitive restriction enzyme;
   (c) thermally inactivating the methylation-sensitive restriction enzyme; and
   (d) amplifying the methylated target nucleic acid, whereby after the amplifying step d) or concurrently with the amplifying step d), any amplification product produced in the amplifying step is detected as an indication of the presence or the amount of the methylated target nucleic acid in the sample.

2. The method according to claim 1, wherein the nucleotide with a methylcytosine base in the recognition nucleic acid sequence is flanked at the 3' side by a nucleotide with a guanine base, wherein said nucleotide with a guanine base is part or is not part of the recognition nucleic acid sequence.

3. The method according to claim 1, whereby the non-methylated contaminant target nucleic acid is originally present in or introduced into the sample.

4. The method according to claim 1, whereby the non-methylated contaminant target nucleic acid is originally present in or introduced into the sample before, during or after step a) of the method according to claim 1 or before or during step b) of the method according to claim 1.

5. The method according to claim 1, wherein the methylation-sensitive restriction enzyme is selected from the group consisting of the restriction enzymes Acl, BsiW I, BspD I, Bst BI, BstU I, Cla I, HpyCH4 IV, Mlu I, Nru I, Pvu I, SnaB I and an isoschizomer thereof or is selected from the group consisting of the restriction enzymes Bsm F I, BstZ I, Dpn II, Eci I, EcoR I, EcoR V, Hpa I, Mbo I, Ple I, Pme I, Rsa I, Sal I, Sau3A I and an isoschizomer thereof.

6. The method according to claim 1, wherein said inactivating step c) and said amplifying step d) are carried out in the same step.

7. The method according to claim 1, wherein amplification reagents for use in the amplifying step d) and the restriction enzyme are combined with the sample before the amplifying step d).

8. The method according to claim 7, wherein the amplification reagents for use in said amplifying step d) and the methylation-sensitive restriction enzyme are combined as a mixture with the sample.

9. The method according to claim 7, wherein the amplification reagents comprise nucleotides, a pair of primers, a probe or a DNA polymerase.

10. A method for amplification of a sample comprising a methylated target nucleic acid, and decontamination of the sample by removal of non-methylated contaminant target nucleic acid, the method consisting of the following steps in the sequence set forth:
   (a) performing a bisulfite reaction on the sample, thereby converting a non-methylated cytosine base into a uracil base while not converting a methylcytosine base, wherein the methylated target nucleic acid comprises at least one nucleotide with a methylcytosine base in a recognition nucleic acid sequence of a restriction enzyme;
   wherein step a) is performed by the substeps of
   a1) mixing the sample comprising the methylated target nucleic acid with a solution comprising sulfite ions;
   a2) incubating the solution obtained in step a1) comprising the methylated target nucleic acid and sulfite ions whereby the target nucleic acid is deaminated;
   a3) incubating the deaminated nucleic acid under alkaline conditions whereby the deaminated nucleic acid is desulfonated, and a4) desalting the deaminated nucleic acid;
(b) adding a methylation-sensitive restriction enzyme to the sample which digests the non-methylated contaminant target nucleic acid, whereby after digestion the non-methylated contaminant target nucleic acid is no longer able to be amplified and the sample is decontaminated, whereby the methylated target nucleic acid is not digested by the methylation-sensitive restriction enzyme;
(c) thermally inactivating the methylation-sensitive restriction enzyme; and
(d) amplifying the methylated target nucleic acid,
whereby after the amplifying step d) or concurrently with the amplifying step d), any amplification product produced in the amplifying step is detected as an indication of the presence or the amount of the methylated target nucleic acid in the sample.

11. The method according to claim 10, characterized in that the concentration of the sulfite ions is 0.1 to 8 M.

12. The method according to claim 10, characterized in that the pH of the solutions in step a1) and a2) are acidic.

13. The method according to claim 10, characterized in that the incubation temperature in step a2) and a3) is between 0° C. to 90° C.

14. The method according to claim 10, characterized in that the incubation time in step a2) is between 30 min to 48 hours.

15. The method according to claim 10, characterized in that the step a3) alkaline conditions are achieved by adding an alkaline solution or buffer.

16. The method according to claim 10, characterized in that the incubation time in step a3) is between 5 min to 60 min.

* * * * *

SEQUENCE LISTING

<160> NUMBER OF SEQ ID NOS: 5

<210> SEQ ID NO 1
<211> LENGTH: 13
<212> TYPE: DNA
<213> ORGANISM: Homo sapiens

<400> SEQUENCE: 1
tgcggtcgac gtt                                                          13

<210> SEQ ID NO 2
<211> LENGTH: 13
<212> TYPE: DNA
<213> ORGANISM: Homo sapiens

<400> SEQUENCE: 2
gccgaccgct ctt                                                          13

<210> SEQ ID NO 3
<211> LENGTH: 17
<212> TYPE: DNA
<213> ORGANISM: Homo sapiens
<220> FEATURE:
<221> NAME/KEY: misc_feature -continued

```
<222> LOCATION: (17)..(17)
<223> OTHER INFORMATION: Nucleotide coupled to fluorescein label

<400> SEQUENCE: 3
cggtcgtcgg ggttggg                                                  17

<210> SEQ ID NO 4
<211> LENGTH: 16
<212> TYPE: DNA
<213> ORGANISM: Homo sapiens
<220> FEATURE:
<221> NAME/KEY: misc_feature
<222> LOCATION: (1)..(1)
<223> OTHER INFORMATION: Nucleotide coupled to LC Red 640 dye
<220> FEATURE:
<221> NAME/KEY: misc_feature
<222> LOCATION: (16)..(16)
<223> OTHER INFORMATION: Nucleotide derivatized with a phosphate group

<400> SEQUENCE: 4
cggcgggagt tcgcgg                                                   16

<210> SEQ ID NO 5
<211> LENGTH: 81
<212> TYPE: DNA
<213> ORGANISM: Homo sapiens
<220> FEATURE:
<221> NAME/KEY: misc_feature
<222> LOCATION: (3)..(3)
<223> OTHER INFORMATION: Cytosine Base methylated before PCR in the
      bisulfite treated target but no longer in the amplicon
<220> FEATURE:
<221> NAME/KEY: misc_feature
<222> LOCATION: (7)..(7)
<223> OTHER INFORMATION: Cytosine Base methylated before PCR in the
      bisulfite treated target but no longer in the amplicon
<220> FEATURE:
<221> NAME/KEY: misc_feature
<222> LOCATION: (10)..(10)
<223> OTHER INFORMATION: Cytosine Base methylated before PCR in the
      bisulfite treated target but no longer in the amplicon
<220> FEATURE:
<221> NAME/KEY: misc_feature
<222> LOCATION: (14)..(14)
<223> OTHER INFORMATION: Cytosine Base methylated before PCR in the
      bisulfite treated target but no longer in the amplicon
<220> FEATURE:
<221> NAME/KEY: misc_feature
<222> LOCATION: (24)..(24)
<223> OTHER INFORMATION: Cytosine Base methylated before PCR in the
      bisulfite treated target but no longer in the amplicon
<220> FEATURE:
<221> NAME/KEY: misc_feature
<222> LOCATION: (28)..(28)
<223> OTHER INFORMATION: Cytosine Base methylated before PCR in the
      bisulfite treated target but no longer in the amplicon
<220> FEATURE:
<221> NAME/KEY: misc_feature
<222> LOCATION: (31)..(31)
<223> OTHER INFORMATION: Cytosine Base methylated before PCR in the
      bisulfite treated target but no longer in the amplicon
<220> FEATURE:
<221> NAME/KEY: misc_feature
<222> LOCATION: (43)..(43)
<223> OTHER INFORMATION: Cytosine Base methylated before PCR in the
      bisulfite treated target but no longer in the amplicon
<220> FEATURE:
<221> NAME/KEY: misc_feature
<222> LOCATION: (46)..(46)
<223> OTHER INFORMATION: Cytosine Base methylated before PCR in the
      bisulfite treated target but no longer in the amplicon
<220> FEATURE:
<221> NAME/KEY: misc_feature
<222> LOCATION: (54)..(54)
<223> OTHER INFORMATION: Cytosine Base methylated before PCR in the
      bisulfite treated target but no longer in the amplicon
```

```
-continued
<220> FEATURE:
<221> NAME/KEY: misc_feature
<222> LOCATION: (56)..(56)
<223> OTHER INFORMATION: Cytosine Base methylated before PCR in the
      bisulfite treated target but no longer in the amplicon
<220> FEATURE:
<221> NAME/KEY: misc_feature
<222> LOCATION: (74)..(74)
<223> OTHER INFORMATION: Cytosine Base methylated before PCR in the
      bisulfite treated target but no longer in the amplicon
<220> FEATURE:
<221> NAME/KEY: misc_feature
<222> LOCATION: (78)..(78)
<223> OTHER INFORMATION: Cytosine Base methylated before PCR in the
      bisulfite treated target but no longer in the amplicon
<220> FEATURE:
<221> NAME/KEY: misc_feature
<222> LOCATION: (81)..(81)
<223> OTHER INFORMATION: Cytosine Base methylated before PCR in the
      bisulfite treated target but no longer in the amplicon

<400> SEQUENCE: 5
tgcggtcgac gttcggggtg tagcggtcgt cggggttggg gtcggcggga gttcgcggga    60 tttttagaa gagcggtcgg c                                               81
```